(12) United States Patent
Zhou et al.

(10) Patent No.: US 11,915,444 B2
(45) Date of Patent: Feb. 27, 2024

(54) SINGLE-PASS PRIMARY ANALYSIS

(71) Applicant: Element Biosciences, Inc., San Diego, CA (US)

(72) Inventors: Chunhong Zhou, San Diego, CA (US); Semyon Kruglyak, San Diego, CA (US); Francisco Garcia, San Diego, CA (US); Minghao Guo, San Diego, CA (US); Haosen Wang, San Diego, CA (US); Ryan Kelly, San Diego, CA (US)

(73) Assignee: Element Biosciences, Inc., San Diego, CA (US)

( * ) Notice: Subject to any disclaimer, the term of this patent is extended or adjusted under 35 U.S.C. 154(b) by 0 days.

(21) Appl. No.: 17/854,042

(22) Filed: Jun. 30, 2022

(65) Prior Publication Data

US 2022/0405523 A1  Dec. 22, 2022

Related U.S. Application Data (63) Continuation of application No. 17/547,602, filed on Dec. 10, 2021, now Pat. No. 11,397,870, which is a
(Continued)

(51) Int. Cl.
*G06T 7/66* (2017.01)
*G06T 7/30* (2017.01)
(Continued)

(52) U.S. Cl.
CPC ............ *G06T 7/66* (2017.01); *G06F 18/232* (2023.01); *G06T 7/30* (2017.01); *G06V 10/751* (2022.01);
(Continued)

(58) Field of Classification Search
CPC ......... G01N 15/147; G02B 7/28; C07K 1/047
See application file for complete search history.

(56) References Cited

U.S. PATENT DOCUMENTS 5,159,403 A * 10/1992 Kosaka ............... G01N 15/1463
356/73
5,558,991 A    9/1996 Trainor
(Continued)

FOREIGN PATENT DOCUMENTS

CN    108203847 B    1/2022
WO    2006084132 A2   8/2006
(Continued)

OTHER PUBLICATIONS

Bo Wang et al.; "An adaptive decorrelation method removes Illumina DNA base-calling errors caused by crosstalk between adjacent clusters"; Scientific Reports; www.nature.com/scientificreports; Published Feb. 20, 2017; 11 pages.
(Continued)

*Primary Examiner* — Yosef Kassa
(74) *Attorney, Agent, or Firm* — Sterne, Kessler, Goldstein & Fox P.L.L.C.

(57) ABSTRACT

Methods and systems for image analysis are provided, and in particular for identifying a set of base-calling locations in a flow cell for DNA sequencing. These include capturing flow cell images after each sequencing step performed on the flow cell, and identifying candidate cluster centers in at least one of the flow cell images. Intensities are determined for each candidate cluster center in a set of flow cell images. Purities are determined for each candidate cluster center based on the intensities. Each candidate cluster center with a purity greater than the purity of the surrounding candidate cluster centers within a distance threshold is added to a template set of base-calling locations.

20 Claims, 4 Drawing Sheets

Related U.S. Application Data continuation of application No. 17/219,556, filed on Mar. 31, 2021, now Pat. No. 11,200,446.

(60) Provisional application No. 63/072,649, filed on Aug. 31, 2020.

(51) Int. Cl.
  *G06V 10/75* (2022.01)
  *G06V 20/69* (2022.01)
  *G06F 18/232* (2023.01)
  *G06V 10/762* (2022.01)

(52) U.S. Cl.
  CPC ............ *G06V 10/763* (2022.01); *G06V 20/69* (2022.01); *G06V 20/693* (2022.01); *G06V 20/695* (2022.01); *G06V 2201/04* (2022.01)

(56) References Cited

U.S. PATENT DOCUMENTS

| | | | |
|---|---|---|---|
| 5,786,894 A * | 7/1998 | Shields | G01N 33/343 356/338 |
| 6,608,682 B2 * | 8/2003 | Ortyn | G01N 15/147 356/417 |
| 6,975,400 B2 * | 12/2005 | Ortyn | G02B 7/28 356/417 |
| 7,019,834 B2 * | 3/2006 | Sebok | G01N 15/147 382/199 |
| 7,170,050 B2 | 1/2007 | Turner et al. | |
| 7,211,390 B2 | 5/2007 | Rothberg et al. | |
| 7,244,559 B2 | 7/2007 | Rothberg et al. | |
| 7,264,929 B2 | 9/2007 | Rothberg et al. | |
| 7,279,338 B2 | 10/2007 | Kim et al. | |
| 7,302,146 B2 | 11/2007 | Turner et al. | |
| 7,315,357 B2 * | 1/2008 | Ortyn | G02B 7/28 356/73 |
| 7,405,281 B2 | 7/2008 | Xu et al. | |
| 7,450,229 B2 * | 11/2008 | Ortyn | G01J 3/2889 356/73 |
| 7,522,757 B2 | 4/2009 | Tsipouras et al. | |
| 7,566,537 B2 | 7/2009 | Balasubramanian et al. | |
| 7,584,857 B2 | 9/2009 | Bohm et al. | |
| 7,640,112 B2 | 12/2009 | Tsipouras et al. | |
| 7,671,987 B2 | 3/2010 | Padmanabhan et al. | |
| 7,674,309 B2 | 3/2010 | Gargano et al. | |
| 7,723,116 B2 | 5/2010 | Evans et al. | |
| 7,745,221 B2 | 6/2010 | Butler et al. | |
| 7,890,157 B2 | 2/2011 | Jo et al. | |
| 8,045,788 B2 | 10/2011 | Watkins et al. | |
| 8,184,298 B2 * | 5/2012 | Popescu | G01N 15/1434 356/450 |
| 8,189,900 B2 | 5/2012 | Sammak et al. | |
| 8,426,209 B2 | 4/2013 | Butler et al. | |
| 8,465,922 B2 | 6/2013 | Eid et al. | |
| 8,526,704 B2 | 9/2013 | Dobbe | |
| 8,617,538 B2 * | 12/2013 | Zoldhelyi | G01N 33/57492 435/325 |
| 8,760,756 B2 * | 6/2014 | Price | G02B 21/244 359/368 |
| 8,885,912 B2 | 11/2014 | Sui | |
| 9,068,916 B2 | 6/2015 | Heng | |
| 9,383,320 B2 * | 7/2016 | Naito | G01N 15/147 |
| 9,591,268 B2 * | 3/2017 | Stoops | G06T 7/73 |
| 10,152,776 B2 | 12/2018 | Langlois et al. | |
| 10,246,744 B2 | 4/2019 | Vijayan et al. | |
| 10,304,189 B2 | 5/2019 | Garcia et al. | |
| 10,689,696 B2 | 6/2020 | Belitz et al. | |
| 10,724,069 B2 * | 7/2020 | Chen | A61B 5/150412 |
| 11,111,487 B2 | 9/2021 | Jovanovich et al. | |
| 11,200,446 B1 | 12/2021 | Zhou et al. | |
| 11,220,707 B1 | 1/2022 | Arslan et al. | |
| 11,397,870 B2 | 7/2022 | Zhou et al. | |
| 11,492,662 B2 | 11/2022 | Glezer et al. | |
| 2003/0224419 A1 | 12/2003 | Corcoran et al. | |
| 2014/0170679 A1 * | 6/2014 | Aitchison | G01N 21/6456 435/287.2 |
| 2016/0102348 A1 | 4/2016 | Donnet | |
| 2018/0274023 A1 | 9/2018 | Belitz et al. | |
| 2019/0130999 A1 | 5/2019 | Oppenheim et al. | |
| 2020/0080141 A1 | 3/2020 | Weng et al. | |
| 2020/0194098 A1 | 6/2020 | Hannigan et al. | |
| 2020/0211673 A1 | 7/2020 | Biggins et al. | |
| 2020/0291454 A1 | 9/2020 | Belhocine et al. | |
| 2020/0308576 A1 | 10/2020 | Badenhorst et al. | |
| 2020/0327377 A1 | 10/2020 | Jaganathan et al. | |
| 2020/0392574 A1 | 12/2020 | Drmanac et al. | |
| 2021/0150715 A1 | 5/2021 | Garcia et al. | |

FOREIGN PATENT DOCUMENTS

| | | |
|---|---|---|
| WO | 2012003374 A2 | 1/2012 |
| WO | 2014196863 A1 | 12/2014 |
| WO | 2016124600 A1 | 8/2016 |
| WO | 2019068797 A1 | 4/2019 |
| WO | 2020/191389 A1 | 9/2020 |

OTHER PUBLICATIONS

International Search Report and Written Opinion of the International Searching Authority directed to International Patent Application No. PCT/US2022/052448, dated May 15, 2023; 16 pages.

N. Whiteford et al., "Swift: primary data analysis for the Illumina Solexa sequencing platform," Bioinformatics, vol. 25, No. 17, published Jun. 23, 2009; pp. 2194-2199.

Anonymous: "MISEQ: Imaging and Base Calling," available at https://support.illumina.com/training.html; video slides presented by Jeremy Peirce 2013, with attached transcript. 30 pages.

International Search Report and Written Opinion of the International Searching Authority directed to International Patent Application No. PCT/US22/52449, dated Mar. 8, 2023; 24 pages.

International Search Report and Written Opinion of the International Searching Authority directed to International Patent Application No. PCT/US2023/063734, dated Jul. 17, 2023; 10 pages.

International Search Report and Written Opinion of the International Searching Authority directed to International Patent Application No. PCT/US2023/063736, dated Aug. 21, 2023; 16 pages.

Korostin Dmitriy et al: "Comparative analysis of novel MGISEQ-2000 sequencing platform vs Illumina HiSeq 2500 for whole-genome sequencing", PLOS One, vol. 15, No. 3, Mar. 16, 2020; 39 pages.

* cited by examiner

SINGLE-PASS PRIMARY ANALYSIS

CROSS-REFERENCE TO RELATED APPLICATIONS

This application is a continuation of U.S. patent application Ser. No. 17/547,602, filed Dec. 10, 2021, which is a continuation of U.S. patent application Ser. No. 17/219,556, filed on Mar. 31, 2021, which claims benefit to U.S. Provisional Patent Application Ser. No. 63/072,649, filed Aug. 31, 2020, each of which is hereby incorporated by reference.

TECHNICAL FIELD

This disclosure relates generally to image data analysis, and particularly to identifying cluster locations for performing base-calling in a digital image of a flow cell during DNA sequencing.

BACKGROUND

Next generation sequencing-by-synthesis using a flow cell may be used for identifying sequences of DNA. As single-stranded DNA fragments from a sequencing library are flooded across a flow cell, the fragments will randomly attach to the surface of the flow cell, typically due to complementary oligomers bound to the surface of the flow cell or beads present thereon. An amplification process is then performed on the DNA fragments, such that copies of a given fragment form a cluster or polony of denatured, cloned nucleotide strands. In some embodiments, a single bead may contain a cluster, and the beads may attach to the flow cell at random locations.

In order to identify the sequence of the strands, the strand pairs are re-built, one nucleotide base at a time. During each base-building cycle, a mixture of single nucleotides, each attached to a fluorescent label (or tag) and a blocker, is flooded across the flow cell. The nucleotides attach at complementary positions on the strands. Blockers are included so that only one base will attach to any given strand during a single cycle. The flow cell is exposed to excitation light, exciting the labels and causing them to fluoresce. Because the cloned strands are clustered together, the fluorescent signal for any one fragment is amplified by the signal from its cloned counterparts, such that the fluorescence for a cluster may be recorded by an imager. After the flow cell is imaged, blockers are cleaved and washed from the flowed nucleotides, more nucleotides are flooded over the flow cell, and the cycle repeats. At each flow cycle, one or more images are recorded.

A base-calling algorithm is applied to the recorded images to "read" the successive signals from each cluster, and convert the optical signals into an identification of the nucleotide base sequence added to each fragment. Accurate base-calling requires accurate identification of the cluster centers, to ensure that successive signals are attributed to the correct fragment.

BRIEF SUMMARY

Provided herein are system, apparatus, article of manufacture, method and/or computer program product embodiments, and/or combinations and sub-combinations thereof which computationally improve resolution of an imager beyond its physical resolution limit and/or provide higher-accuracy source location in an image.

As a particular application of such, embodiments of methods and systems for identifying a set of base-calling locations in a flow cell are described. These include capturing flow cell images after each flow cycle, and identifying candidate cluster centers in at least one of the flow cell images. Intensities are determined for each candidate cluster center. Purities are determined for each candidate cluster center based on the intensities. In some embodiment, intensities and/or purities are determined at a sub-pixel level. Each candidate cluster center with a purity greater than the purity of the surrounding candidate cluster centers within a distance threshold is added to a set of base-calling locations. The set of base-calling locations may be referred to herein as a template.

In some embodiments, identifying the candidate cluster centers includes labeling each pixel of the flow cell image as a candidate cluster center.

In some embodiments, identifying the candidate cluster centers includes detecting a set of potential cluster center locations using a spot-finding algorithm and then identifying additional cluster locations around each potential cluster center location.

Further embodiments, features, and advantages of the present disclosure, as well as the structure and operation of the various embodiments of the present disclosure, are described in detail below with reference to the accompanying drawings.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the art(s) to make and use the embodiments.

In the drawings, like reference numbers generally indicate identical or similar elements. Additionally, generally, the left-most digit(s) of a reference number identifies the drawing in which the reference number first appears.

DETAILED DESCRIPTION

Provided herein are system, apparatus, article of manufacture, method and/or computer program product embodiments, and/or combinations and sub-combinations thereof which computationally improve resolution of an imager beyond its physical resolution limit and/or provide higher-accuracy source location in an image. The image processing techniques described herein are particularly useful for base-calling in next generation sequencing, and base-calling will be used as the primary example herein for describing the application of these techniques. However, such imaging analysis techniques may also be particularly useful in other applications where spot-detection and/or CCD imaging is used. For example, identifying the actual center (e.g., source location) of a perceived optical signal has utility in numerous other fields, such as location detection and tracking, astronomical imaging, heat mapping, etc. Additionally, such techniques as described herein may be useful in any other application benefiting from increasing resolution computationally once the physical resolution limits of an imager have been reached.

In DNA sequencing, identifying the centers of clusters or polonies (which are often formed on beads) is sometimes referred to as primary analysis. Primary analysis involves the formation of a template for the flow cell. The template includes the estimated locations of all detected clusters in a common coordinate system. Templates are generated by identifying cluster locations in all images in the first few flows of the sequencing process. The images may be aligned across all the images to provide the common coordinate system. Cluster locations from different images may be merged based on proximity in the coordinate system. Once the template is generated, all further images are registered against it and the sequencing is performed based on the cluster locations in the template.

A variety of algorithms exist for identifying cluster centers in an image. These existing algorithms suffer from a number of shortcomings. As discussed above, cluster centers may appear merged if they are close together. The proximity may be due to precision issues or registration problems. Different clusters may thus be treated as a single cluster, resulting in improper sequence identification or missing out on a sequence.

Additionally, algorithms may require finding clusters across several images to identify the cluster locations for the template. This may require excessive processing time.

Figure 1:
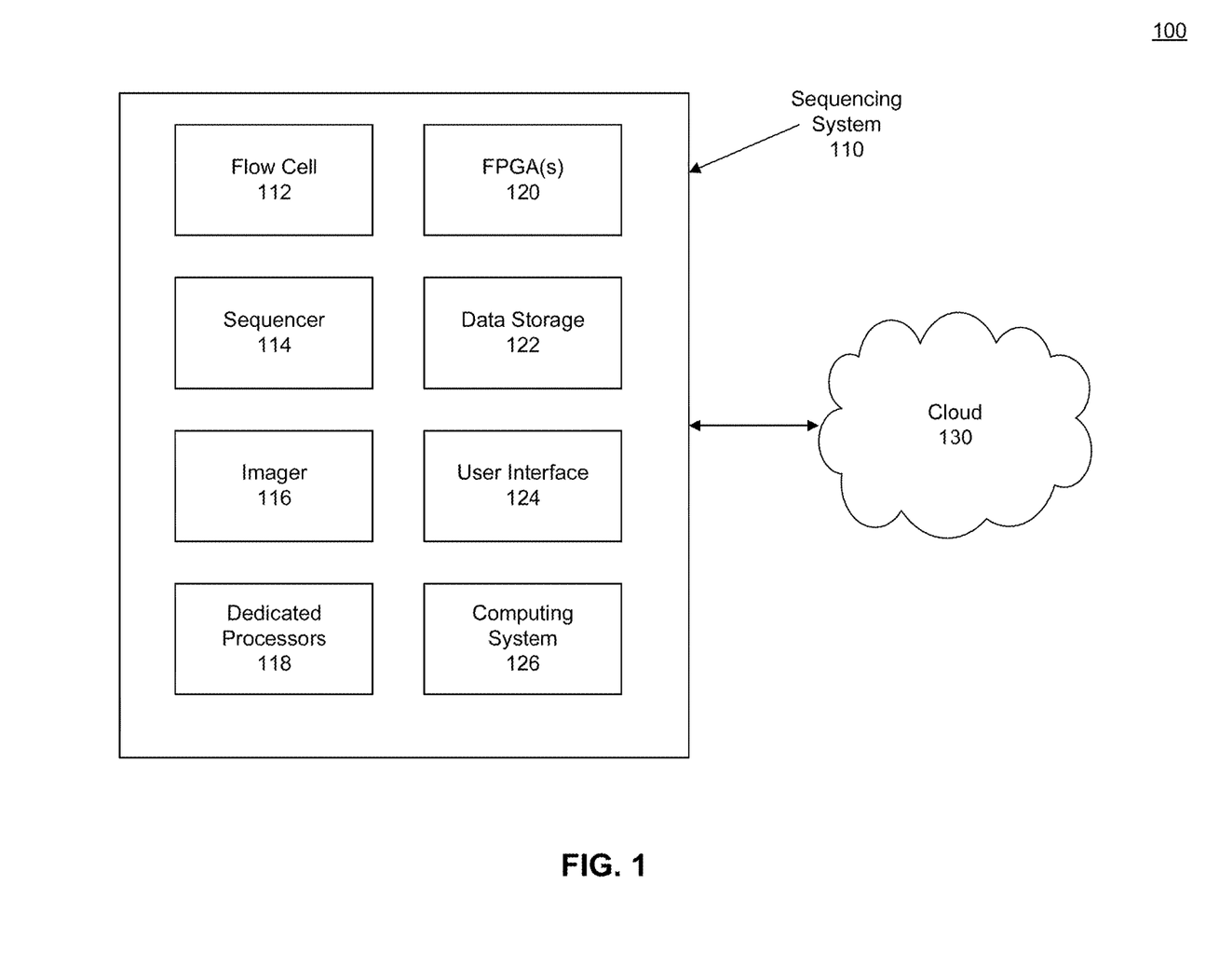
FIG. 1 illustrates a block diagram of a system for identifying cluster locations on a flow cell, according to some embodiments

FIG. 1 illustrates a block diagram of a system 100 for identifying cluster locations on a flow cell, according to an embodiment. The system 100 has a sequencing system 110 that may include a flow cell 112, a sequencer 114, an imager 116, data storage 122, and user interface 124. The sequencing system 110 may be connected to a cloud 130. The sequencing system 110 may include one or more of dedicated processors 118, Field-Programmable Gate Array(s) (FPGA(s)) 120, and a computer system 126.

In some embodiments, the flow cell 112 is configured to capture DNA fragments and form DNA sequences for base-calling on the flow cell. The sequencer 114 may be configured to flow a nucleotide mixture onto the flow cell 112, cleave blockers from the nucleotides in between flowing steps, and perform other steps for the formation of the DNA sequences on the flow cell 112. The nucleotides may have fluorescent elements attached that emit light or energy in a wavelength that indicates the type of nucleotide. Each type of fluorescent element may correspond to a particular nucleotide base (e.g., A, G, C, T). The fluorescent elements may emit light in visible wavelengths.

For example, each nucleotide base may be assigned a color. Adenine may be red, cytosine may be blue, guanine may be green, and thymine may be yellow, for example. The color or wavelength of the fluorescent element for each nucleotide may be selected so that the nucleotides are distinguishable from one another based on the wavelengths of light emitted by the fluorescent elements.

The imager 116 may be configured to capture images of the flow cell 112 after each flowing step. In an embodiment, the imager 116 is a camera configured to capture digital images, such as a CMOS or a CCD camera. The camera may be configured to capture images at the wavelengths of the fluorescent elements bound to the nucleotides.

The resolution of the imager 116 controls the level of detail in the flow cell images, including pixel size. In existing systems, this resolution is very important, as it controls the accuracy with which a spot-finding algorithm identifies the cluster centers. One way to increase the accuracy of spot finding is to improve the resolution of the imager 116, or improve the processing performed on images taken by imager 116. The methods described herein may detect cluster centers in pixels other than those detected by a spot-finding algorithm. These methods allow for improved accuracy in detection of cluster centers without increasing the resolution of the imager 116. The resolution of the imager may even be less than existing systems with comparable performance, which may reduce the cost of the sequencing system 110.

In an embodiment, the images of the flow cell may be captured in groups, where each image in the group is taken at a wavelength or in a spectrum that matches or includes only one of the fluorescent elements. In another embodiment, the images may be captured as single images that captures all of the wavelengths of the fluorescent elements.

The sequencing system 100 may be configured to identify cluster locations on the flow cell 112 based on the flow cell images. The processing for identifying the cluster may be performed by the dedicated processors 118, the FPGA(s) 120, the computing system 126, or a combination thereof. Identifying or determining the cluster locations may involve performing traditional cluster finding in combination with the cluster finding methods described more particularly herein.

General purpose processors provide interfaces to run a variety of program in an operating system, such as Windows™ or Linux™. Such an operating system typically provides great flexibility to a user.

In some embodiments, the dedicated processors 118 may be configured to perform steps of the cluster finding methods described herein. They may not be general-purpose processors, but instead custom processors with specific hardware or instructions for performing those steps. Dedicated processors directly run specific software without an operating system. The lack of an operating system reduces overhead, at the cost of the flexibility in what the processor may perform. A dedicated processor may make use of a custom programming language, which may be designed to operate more efficiently than the software run on general purpose processors. This may increase the speed at which the steps are performed and allow for real time processing.

In some embodiments, the FPGA(s) 120 may be configured to perform steps of the cluster finding methods described herein. An FPGA is programmed as hardware that will only perform a specific task. A special programming language may be used to transform software steps into hardware componentry. Once an FPGA is programmed, the hardware directly processes digital data that is provided to it without running software. The FPGA instead uses logic gates and registers to process the digital data. Because there is no overhead required for an operating system, an FPGA generally processes data faster than a general purpose processors. Similar to dedicated processors, this is at the cost of flexibility.

The lack of software overhead may also allow an FPGA to operate faster than a dedicated processor, although this will depend on the exact processing to be performed and the specific FPGA and dedicated processor.

A group of FPGA(s) 120 may be configured to perform the steps in parallel. For example, a number of FPGA(s) 120 may be configured to perform a processing step for an image, a set of images, or a cluster location in one or more images. Each FPGA(s) 120 may perform its own part of the processing step at the same time, reducing the time needed to process data. This may allow the processing steps to be completed in real time. Further discussion of the use of FPGAs is provided below.

Performing the processing steps in real time may allow the system to use less memory, as the data may be processed as it is received. This improves over conventional systems may need to store the data before it may be processed, which may require more memory or accessing a computer system located in the cloud 130.

In some embodiments, the data storage 122 is used to store information used in the identification of the cluster locations. This information may include the images themselves or information derived from the images captured by the imager 116. The DNA sequences determined from the base-calling may be stored in the data storage 122. Parameters identifying cluster locations may also be stored in the data storage 122.

The user interface 124 may be used by a user to operate the sequencing system or access data stored in the data storage 122 or the computer system 126.

The computer system 126 may control the general operation of the sequencing system and may be coupled to the user interface 124. It may also perform steps in the identification of cluster locations and base-calling. In some embodiments, the computer system 126 is a computer system 400, as described in more detail in FIG. 4. The computer system 126 may store information regarding the operation of the sequencing system 110, such as configuration information, instructions for operating the sequencing system 110, or user information. The computer system 126 may be configured to pass information between the sequencing system 110 and the cloud 130.

As discussed above, the sequencing system 110 may have dedicated processors 118, FPGA(s) 120, or the computer system 126. The sequencing system may use one, two, or all of these elements to accomplish necessary processing described above. In some embodiments, when these elements are present together, the processing tasks are split between them. For example, the FPGA(s) 120 may be used to perform the cluster center finding methods described herein, while the computer system 126 may perform other processing functions for the sequencing system 110. Those skilled in the art will understand that various combinations of these elements will allow various system embodiments that balance efficiency and speed of processing with cost of processing elements.

The cloud 130 may be a network, remote storage, or some other remote computing system separate from the sequencing system 110. The connection to cloud 130 may allow access to data stored externally to the sequencing system 110 or allow for updating of software in the sequencing system 110.

Figure 3:
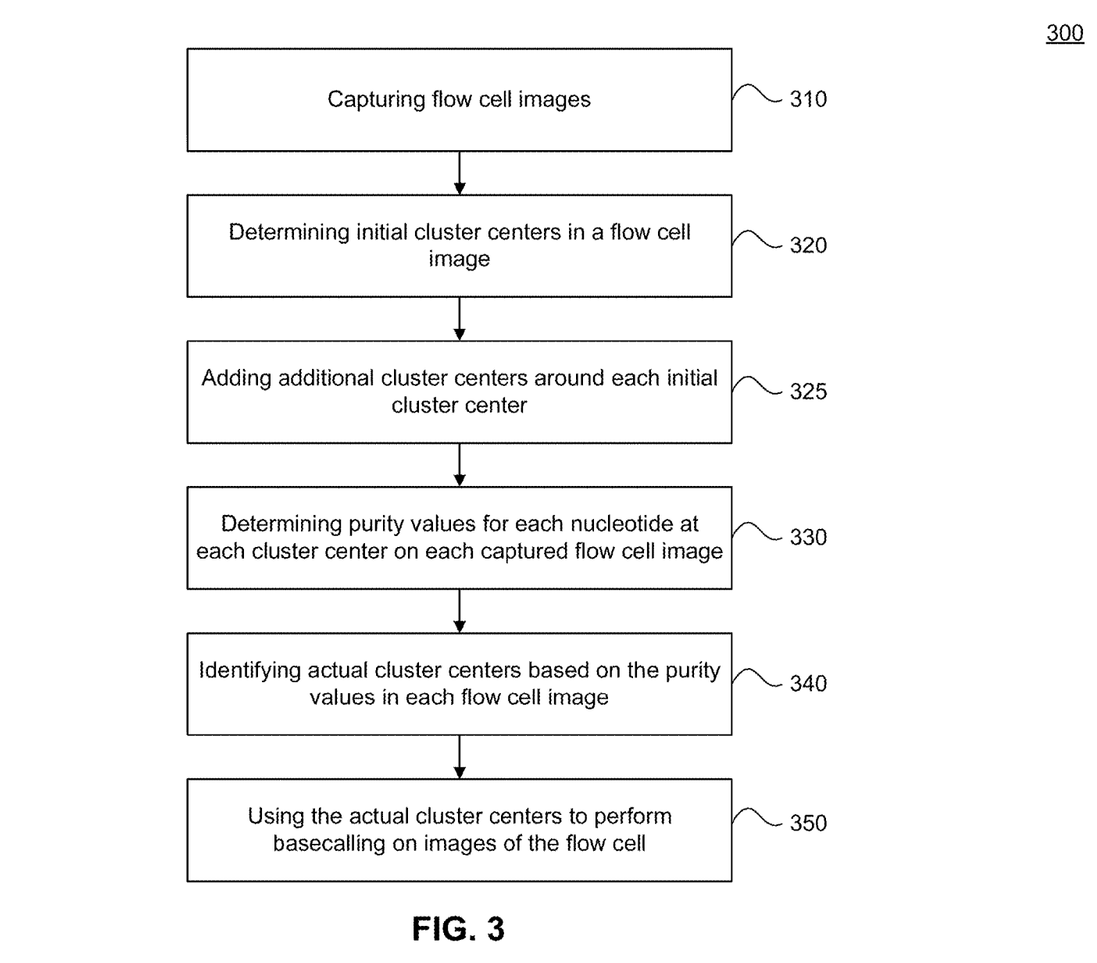
FIG. 3 is a flow chart illustrating a method for identifying locations at which to perform base-calling, according to some embodiments.

FIG. 3 is a flow chart illustrating a method 300 for identifying actual cluster center locations at which to perform base-calling. A cluster center in a flow cell image is a location in the image which corresponds to the location of the clonal cluster on the physical flow cell. The wavelength of an optical signal detected at a cluster center correlates to a nucleotide base added to a fragment on the flow cell at that location. In order for a DNA sequence to be determined correctly, the sequentially detected optical signals must be consistently attributed to the correct DNA fragment. Accurately identifying the location of the cluster center thus improves the base-calling accuracy for that fragment. In some embodiments, once the actual cluster centers have been identified, such locations may be mapped onto a template for use in subsequent base-call cycles using the same flow cell. The method 300 may be performed by the dedicated processors 118, the FPGA(s) 120, or the computer system 126.

In step 310, flow cell images are captured. The flow cell images may be captured by imager 116, as discussed above. Step 310 may involve capturing one image at a time to be processed by the following steps, or may involve capturing a set of images for simultaneous processing. In an example where a set of images is captured, each image in the set of images may correspond to a different detected wavelength. For example, given the above notation of colors tied to nucleotides, the set of images may include four images, each corresponding to signals captured at a respective one of red, blue, green, and yellow wavelengths, In an example where a single image is captured, that image may include all the detected wavelengths of interest. Each image or set of images may be captured for a single flowing step on the flow cell. In some embodiments, the flow cell images are captured with reference to a coordinate system.

Figure 2:
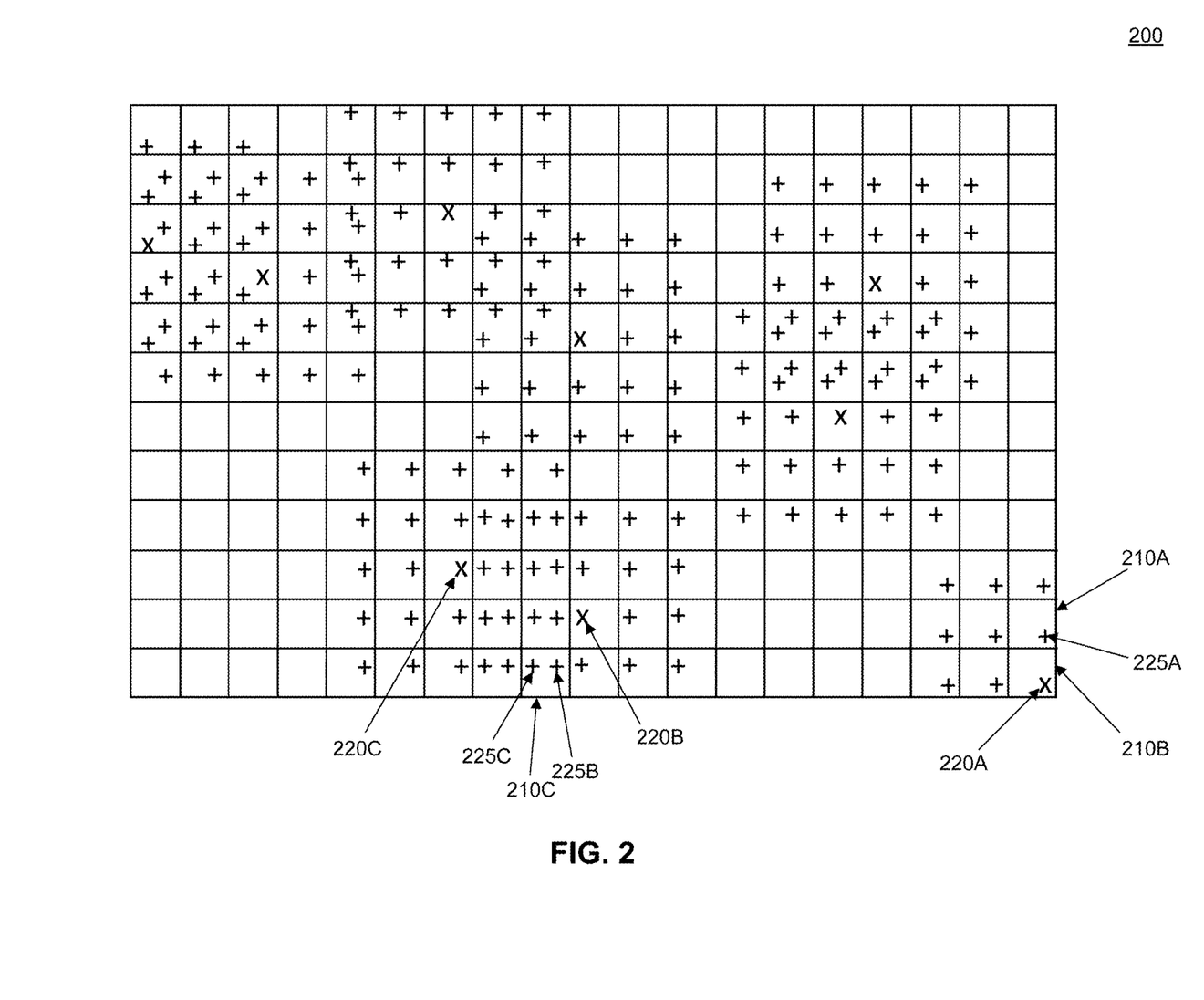
FIG. 2 illustrates an example flow cell image with candidate cluster center centers, according to some embodiments.

FIG. 2 illustrates a schematic of a flow cell image 200 with signals from clusters present thereon. The flow cell image 200 is made up of pixels 210, such as pixels 210A, 210B, and 210C. During step 310, the imager records the optical signals received from the flow cell after, for example, excitation of the fluorescent elements bound to fragments on the flow cell, such fragments being located in clonal clusters of fragments.

In step 320, locations of potential cluster centers in the flow cell image are identified. For example, in some embodiments, the optical signals imaged in step 310 may be input into a spot-finding algorithm, such that the spot-finding algorithm outputs a set of potential cluster centers. In some embodiments, the potential cluster centers may be identified using only a single flow cell image (e.g., one image containing all wavelengths of interest). In some other embodiments, the potential cluster centers may be identified from a set of images from a single flowing cycle on the flow cell (e.g., one image at each wavelength of interest). The use of only a flow cell image or set of flow cell images from a single flowing cycle advantageously reduces the amount of processing time, as the spot-finding algorithm need not wait for additional images from future flowing cycles to be obtained.

In still other embodiments, the spot-finding algorithm may be applied to images from more than one flow cycle, and the potential cluster centers may be found using some combination of those images. For example, the potential cluster centers may be identified by the presence of spots occupying the same location in images from more than one flow cycle.

The potential cluster center locations identified by the spot-finding algorithm are depicted with an "X" in FIG. 2, such as potential cluster center locations 220A, 220B, and 220C, Due to the random nature of fragment attachment to the flow cell, some of the clonal clusters may be close together, while other clusters may be further apart or even stand alone. As a result, some "X"s in FIG. 2 are located more closely together than others. Additionally, some pixels may be identified as containing a potential cluster center, while others are not. For example, pixel 210A may be identified as containing a potential cluster center location 220A, while pixel 210B is not initially identified as containing a potential cluster center location 220.

In some embodiments, the spot-finding algorithm may identify the potential cluster center locations 220 at a sub-pixel resolution by interpolating across the pixel 210. For example, the potential cluster center location 220A is located in the lower right side of pixel 210A, rather than the center of pixel 210A. Other potential cluster center locations may be located in different areas of their respective pixels 210. For example, potential cluster center location 220B is located in the top right of a pixel, and potential cluster center location 220C is located in the top left of a pixel. Interpolation may be performed by an interpolation function.

In some embodiments, the interpolation function is a Gaussian interpolation function known to persons of skill in the art. The sub-pixel resolution may allow the potential cluster locations to be determined, for example, at one-tenth pixel resolution, although other resolutions are also considered. In embodiments, for example, the resolution may be one-fourth pixel resolution, one-half pixel resolution, etc. The interpolation function may be configured to determine this resolution.

The interpolation function may be used to fit to the intensity of the light in one or more pixels 210. This interpolation allows the sub-pixel locations to be identified. The interpolation function may be applied across a set of pixels 210 that include a potential cluster center location 220. In an embodiment, the interpolation function may be fit to a pixel 210 with a potential cluster center location 220 in it and the surrounding pixels 210 that touch the edges of that pixel 210.

In some embodiments, the interpolation function may be determined at a number of points in the image. The resolution determines how many points are located in each pixel 210. For example, if the resolution is one-tenth of a pixel, then along a line perpendicular to the pixel edge there will be nine points calculated across the pixel 210 and one on each edge, dividing the pixel 210 into ten parts. In some embodiments, the interpolation function is calculated at each point and the difference between the interpolation function at each point and the pixel intensity is determined. The center of the interpolation function is shifted to minimize the difference between the interpolation function and the intensity in each pixel 210. This sub-pixel interpolation allows the system to achieve a higher resolution with a lower-resolution imager, reducing cost and/or complexity of the system.

In some embodiments, the interpolation may be performed on a five-by-five grid. The grid may be centered on pixel center 210 in a pixel with a potential cluster center location.

While some embodiments of step 320 use a spot-finding algorithm to identify potential cluster center locations, some other embodiments of step 320 initially identify every pixel in the captured flow cell image as a potential cluster center location. For example, in FIG. 2, every pixel 210 may be identified as a potential cluster center location 220. This approach eliminates the need for a spot-finding algorithm, which may simplify the type of processing needed to implement method 300. This approach may be advantageous when massive parallel processing is available, as each potential cluster center location may be processed in parallel. This may reduce processing time, although at the potential cost of additional hardware, such as increased dedicated processors 118 or FPGA(s) 120. In some embodiments, an interpolation function may be then used as described above for identifying intensity at a sub-pixel resolution across the entirety of the flow cell image.

As discussed above, a cluster center identifies a location in the image, such as a pixel 210, which corresponds to the location of the clonal cluster on the physical flow cell. The potential cluster center locations 220 are locations in the image where light at one or more wavelengths is detected by the imager. In some cases, it is possible that the physical location of a cluster corresponds to one set of pixels 210, but that the optical signals from that cluster overflow onto additional pixels 210 that are adjacent to that one set, for example due to saturation of the corresponding sensor within the camera (also referred to as "blooming"). Additionally, when clusters are located close together, the optical signals from those clusters may overlap, even if the clusters themselves do not. Identifying the true cluster centers allows the detected signals to be attributed to the correct DNA fragments, and thus improves the accuracy of the base-calling algorithm.

Accordingly, in step 325, additional cluster signal locations 225 are identified around each potential cluster center location 220. These are depicted with a "+" in FIG. 2, such as 225A, 225B, and 225C. These additional cluster signal locations 225 correspond to other locations in the flow cell which may constitute a cluster center, instead of or in addition to locations already identified as potential cluster center locations 220.

In some embodiments, additional cluster locations 225 are placed around the potential cluster center locations 220. In some embodiments, these additional cluster locations 225 are not initially identified by a spot finding algorithm, but are placed in a pattern around each potential cluster center location 220 that is identified by a spot finding algorithm. The additional cluster locations 225 do not represent actual, detected cluster centers, but rather represent potential locations to check for cluster centers that might otherwise be undetected. Such cluster centers may be undetected due to mixing between signals from proximate cluster centers, errors in the spot finding algorithm, or other effects.

As an example, additional cluster location 225A may be placed in pixel 210A, based on the location of potential cluster center location 220A. In this context, this may mean that the additional cluster location 225A is placed a pixel's width away from the potential cluster center location 220A. Other additional cluster locations 225 are also located around potential cluster center location 220A. It should be understood that additional cluster locations 225 would not be located where pixels 210 do not exist, such as when a potential cluster center location 220 is near the edge of the flow cell image 200.

In some embodiments, the additional cluster signal locations 225 are placed in a grid centered around a potential cluster center location 220. The additional cluster locations 225 may be placed spaced apart from each other and the potential cluster center location 220 by a pixel width. In some embodiments, the additional cluster locations 225 and the potential cluster center location 220 form a square grid. The grid may have an area of five pixels by five pixels, nine by nine, fifteen by fifteen, or other dimensions.

In some embodiments, potential cluster center locations 220 may be close enough together to cause the corresponding grids of additional cluster locations 225 to overlap. This may result in the same pixel 210 containing an additional cluster location 225 from more than one potential cluster center location 220, such that more than one additional cluster location 225 is attributed to the same pixel 210. For example, pixel 210C contains additional cluster location 225B (which was identified based on potential cluster center location 220B), as well as additional cluster location 225C (which was identified base on potential cluster center location 220C).

In some embodiments, if the additional cluster locations 225 in the same pixel 210 are close enough together, one of the additional cluster locations 225 is discarded and the other is used to represent both. The two additional cluster locations 225 may be considered as close enough together for such treatment if they are within, for example and without limitation, two tenths of a pixel, one tenth of a pixel, or some other sub-pixel distance.

One of skill in the art will appreciate that if, in step 320, all pixel locations were identified as potential cluster center locations 220, then step 325 may be skipped as there are no other pixels left in the flow cell image to consider in addition to the identified potential cluster center locations.

In some embodiments, the potential cluster center locations 220 (and the surrounding additional cluster locations 225, if identified) together constitute a set of all candidate cluster centers. These candidate cluster centers may be processed to identify the actual cluster centers for each captured flow cell image.

Accordingly, once the potential cluster center locations 220 and their surrounding grids of additional cluster locations 225 (i.e., the candidate cluster centers) have been identified, they may be used as a starting point for determining the actual locations of the cluster centers, which may or may not be the same as the originally-identified potential cluster center locations 220.

Returning to FIG. 3, in step 330, a purity value for each candidate cluster center on each captured flow cell image is determined. The purity values may be determined based on the wavelengths of the fluorescent elements bound to the nucleotides and the intensity of the pixels in the captured flow cell images.

At each candidate cluster center, the intensity of the pixel is a combination of the energy or light emitted across the spectral bandwidth of the imager. In some embodiments, an amount of energy or light corresponding to the fluorescent spectral bandwidth of each nucleotide base may be found. The purity of each signal corresponding to a particular nucleotide base may be found as a ratio of the amount of energy for one nucleotide base signal to the total amount of energy for each other nucleotide base signal (e.g., the purity of a "red" signal may be determined based on relative intensities of detected red wavelengths for that pixel or sub-pixel as compared to each of detected blue, green, and yellow wavelengths). An overall purity of the pixel may be the largest ratio, the smallest ratio, a mean of the ratios, or a median of the ratios. The calculated purity may then be assigned to that pixel or sub-pixel.

As mentioned above, a set of flow cell images may be captured for a single flow cycle. Each image in the set is captured at a different wavelength, each wavelength corresponding to one of the fluorescent elements bound to the nucleotides. The purity of a given cluster center across the set of images may be the highest, lowest, median, or mean purity from the set of purities for the set of images.

In some embodiments, the purity of a candidate cluster center may be determined as one minus the ratio of the second highest intensity or energy from the wavelengths for a pixel to the highest intensity or energy from the wavelengths for that pixel. A threshold may be set for what constitutes high or low purity. For example, the highest purity may be one and low purity pixels may have purity values closer to zero. The threshold may be set in between.

In some embodiments, the ratio of the two intensities may be modified by adding an offset to both the second highest intensity and the highest intensity. The offset may provide improved accuracy in the quality score. For example, in some cases, the two intensities in the ratio may differ by a small amount of the absolute maximum intensity that is also a large percentage of the highest intensity. As a specific, non-limiting example, the highest intensity may be ten and the lowest intensity may be one with a maximum possible intensity of 1000. The ratio in this case will be 0.1, which results in a purity of 0.9. Without more, this potentially reads as a high quality score. This contrasts with an intensity of, for example, 500 for the highest intensity and 490 for the second highest intensity. This example has about the same absolute difference, but the ratio is close to one and the purity is close to zero. In the first case, the purity is misleading, as the low overall intensity suggests that no polony is present. In the second case, the purity is more accurate and indicates that the pixel is displaying intensity or energy from two different cluster centers that are located nearby.

The offset may be a value added to the intensities in the ratio to resolve such issues. For example, if the offset is ten percent of the maximum amplitude, in the example above, the offset is 100 and the first ratio becomes 101 over 110, which is much closer to one, resulting in a purity near zero, which accurately reflects the small delta between the two wavelength intensities. In the second ratio, the ratio is 600 over 590, which is still close to one, again resulting in a purity near zero.

As another example of incorporating the offset, if the highest intensity is 800 and the lowest intensity is one, the purity without the offset is close to one, as the ratio is almost zero. If the offset is again 100, the ratio becomes 101 over 900. This lowers the purity slightly from one to about 0.89. While this may decrease the purity, the calculated purity is still high. The offset value may be set to reduce this impact. For example, the offset in another case may be 10. Using the previous example of a highest intensity of ten and a lowest intensity of one, the purity because one minus 10/11, or around 0.09, which is accurately reflects the small difference between the intensities. In the example where the highest intensity is 600 and the lowest intensity is 590, the purity is one minus 600/610, or around 0.016, which is again reflective of the small difference between the intensities. In the example where the highest intensity is 800 and the lowest intensity is one, the purity is one minus 11/810, or around 0.99, which is a much smaller decrease in purity and is reflects the large difference between the intensities.

In step 340, the actual cluster centers are identified based on the purity values calculated for the candidate cluster centers for the flow cell. The actual cluster centers may be a subset of the candidate cluster locations identified in steps 320 and 325.

In some embodiments, the actual cluster centers are identified by comparing the purity for each candidate cluster center across the flow cell image to nearby candidate cluster centers within that same image. In some embodiments, given two candidate cluster centers that are being compared, the candidate cluster center with the greater purity is kept. In some embodiments, candidate cluster centers are only compared to other candidate cluster centers within a certain distance. For example, this distance threshold may be based on the pixel size and the size of the clusters of a given nucleotide.

For example, if the average size of a cluster is four pixel widths/heights, then the distance threshold may be two pixel widths/heights, as any candidate cluster centers within two pixel widths/heights of each other likely either belong to the same cluster or have a higher intensity (indicating that the candidate cluster center is actually on the edge of two separate clusters).

In some embodiments where purity is calculated across multiple flow cell cycles, determining that a candidate cluster center consistently has a purity that is higher than the surrounding candidate cluster centers across multiple flow cell images may further strengthen the likelihood that the location is an actual cluster center. Lower purity may indicate that the signal detected in the candidate cluster center is not an actual cluster center, but noise, mixing of other signals, or some other phenomenon.

In step 350, the actual cluster centers are used to perform base-calling on flow cell images. For example, the wavelength detected from an actual cluster center may be determined, which is in turn correlated to a particular nucleotide base (e.g., A, G, C, T). That nucleotide base is then logged as having been added to the sequence corresponding to the actual cluster center.

Through successive iterations of flow cycles and fluorescence wavelength identification at actual cluster centers in successive flow cell images, the sequence for the DNA fragment corresponding to each actual cluster center on the flow cell may be built.

In some embodiments, a template is formed from the actual cluster centers identified for a single flow cycle. The actual cluster locations in the template may then be used to identify where to perform base-calling in images from subsequent flow cycles.

Flow cell images captured in different flow cycles may have registration issues due to shifting in the position of the flow cell or the imager between the flow cycles. Accordingly, in some embodiments, step 350 may include a registration step to properly align successive images. This ensures that the actual cluster centers on the template accurately map to the same locations on each flow cell image, thus improving accuracy of the base-calling.

In some embodiments where a template is used to identify actual cluster centers in subsequent images, only the data corresponding to relevant locations in those subsequent images need be maintained and/or processed. This decrease in the amount of data processed increases the speed and/or efficiency of the processing, such that accurate results may be obtained more quickly than in legacy systems. Additionally, a decrease in the amount of data stored decreases the amount of storage needed for a sequencer, thus decreasing the amount and/or cost of resources needed.

Additionally, some legacy systems require comparing different images to one another to identify cluster locations. This comparison may include applying a spot-finding algorithm to images from multiple flow cell cycles, and then comparing the spot-finding results across the images. This may require storing images or spot-finding results for each of multiple flow cycles. Method 300 may improve the processing and storage efficiency of cluster finding because the images do not need to be compared directly. Instead, the images may be processed in real time and only the purity information and/or final template location need be stored.

The sequencing flow cycle and image creation processes often run faster than the spot-finding and base-calling programs that analyze the images. This disparity in execution time may require storing the flow cell images after each flow cycle, or a delay in the sequencing flow cycle while waiting for some or all of the image analysis processes to complete.

The use of FPGAs allows for increased speed of processing without sacrificing accuracy. Implementing portions or all of the processes described herein on FPGAs reduces processor overhead and may allow for parallel processing on the FPGAs. For example, each possible cluster location may be processed by a different FPGA, or a single FPGA configured to process the possible cluster locations in parallel at the same time. When properly implemented, this may allow for real-time processing. Real-time processing has the advantage that the image may be processed as it is generated. The FPGA will be ready to process the next image by the time the sequencing system has prepared the flow cell. The sequencing system will not need to wait for the post-processing and the entire process of primary analysis may be completed in a fraction of the time. Additionally, because the entire image has been processed as it is received, the only information that need be stored is data for performing base-calling. Instead of storing every image, only the purity or intensity for particular pixels need be stored. This greatly reduces the need for data storage in the sequencing system or for remote storage of the images.

In some embodiments, the entire process, including image registration, intensity extraction, purity calculation, base-calling, and other steps, is performed by FPGAs. This may provide the most compact implementation and provides the speed and throughput necessary for real-time processing.

In some embodiments, the processing responsibilities are shared, such as between the FPGAs and an associated computer system. For example, in some embodiments, the FPGAs may handle image registration, intensity extraction, and purity calculations. Then, the FPGAs then hand the information off to the computer system for base-calling. This approach balances the load between the FPGAs and computer system resources, including scaling down the communication between FPGAs and computer system. It also provides flexibility for software on the computer system to handle base-calling with quick algorithm tune-ups capabilities. Such an approach may provide real-time processing.

Those skilled in the art will recognize that different configurations of the FPGAs, dedicated processors, and the computer system may be used to perform the various steps. The selection of a given configuration may be based on the flow cell image size, imager resolution, the number of images to process, desired accuracy, and the necessary speed. The implementation cost and hardware cost for the FPGAs, dedicated processors, and computer system may also impact the choice of configuration.

As a non-limiting example comparing performance between existing methods and embodiments of the methods described herein, tests were run on two example flow cells, one with a low density of clusters and one with a high density of clusters. For the comparison, the tests were run using each method to target a specific average error rate for false positives on clusters identified.

For the low-density flow cell, the average error rate was 0.3%. Existing methods identified around 78,000 cluster centers, while the methods described herein identified around 98,000 cluster centers. For the high-density flow cell, the average error rate was 1.1%. Existing methods identified around 63,000 cluster centers, while the methods described herein identified around 170,0000 clusters.

The results suggest that the methods described herein effectively identify more clusters than existing methods. Further, even at the same error rate, when the density of the clusters on the flow cell increases, the methods disclosed herein perform even better, identifying almost three times as many clusters. In some embodiments, this may allow for flow cells to be flowed at a higher density without the performance loss that is typically experienced in existing methods. Example Computer System Various embodiments may be implemented, for example, using one or more computer systems, such as computer system 400 shown in FIG. 4. One or more computer systems 400 may be used, for example, to implement any of the embodiments discussed herein, as well as combinations and sub-combinations thereof.

Figure 4:
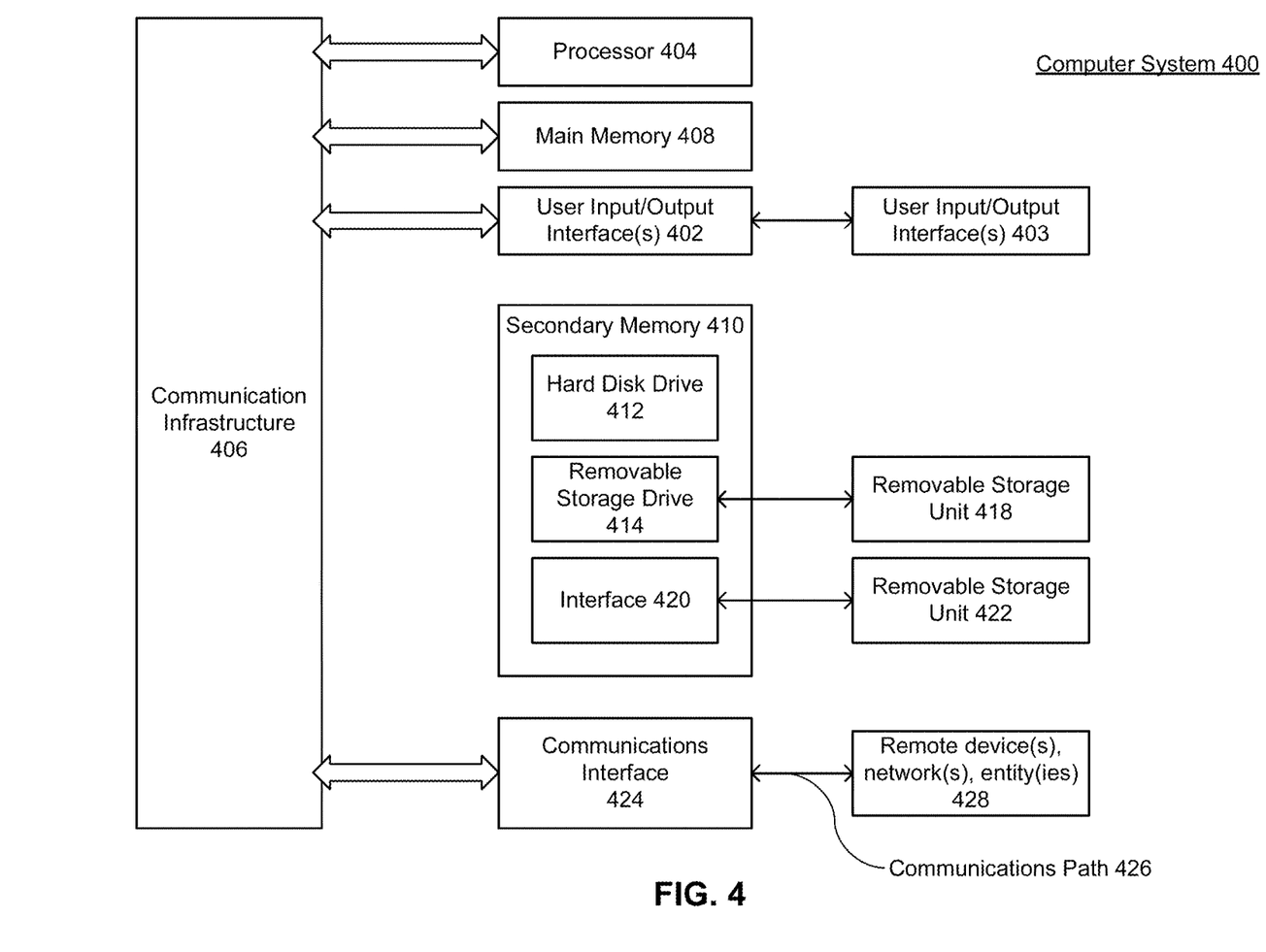
FIG. 4 illustrates a block diagram of a computer that may be used to perform various aspects of the present disclosure, according to some embodiments.

Computer system 400 may include one or more processors (also called central processing units, or CPUs), such as a processor 404. Processor 404 may be connected to a bus or communication infrastructure 406.

Computer system 400 may also include user input/output device(s) 403, such as monitors, keyboards, pointing devices, etc., which may communicate with communication infrastructure 406 through user input/output interface(s) 402. The user input/output devices 403 may be coupled to the user interface 124 in FIG. 1.

One or more of processors 404 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, vector processing, array processing, etc., as well as cryptography (including brute-force cracking), generating cryptographic hashes or hash sequences, solving partial hash-inversion problems, and/or producing results of other proof-of-work computations for some blockchain-based applications, for example. With capabilities of general-purpose computing on graphics processing units (GPGPU), the GPU may be particularly useful in at least the image recognition and machine learning aspects described herein.

Additionally, one or more of processors 404 may include a coprocessor or other implementation of logic for accelerating cryptographic calculations or other specialized mathematical functions, including hardware-accelerated cryptographic coprocessors. Such accelerated processors may further include instruction set(s) for acceleration using coprocessors and/or other logic to facilitate such acceleration.

Computer system 400 may also include a main or primary memory 408, such as random access memory (RAM). Main memory 408 may include one or more levels of cache. Main memory 408 may have stored therein control logic (i.e., computer software) and/or data.

Computer system 400 may also include one or more secondary storage devices or secondary memory 410. Secondary memory 410 may include, for example, a main storage drive 412 and/or a removable storage device or drive 414. Main storage drive 412 may be a hard disk drive or solid-state drive, for example. Removable storage drive 414 may be a floppy disk drive, a magnetic tape drive, a compact disk drive, an optical storage device, tape backup device, and/or any other storage device/drive.

Removable storage drive 414 may interact with a removable storage unit 418. Removable storage unit 418 may include a computer usable or readable storage device having stored thereon computer software (control logic) and/or data. Removable storage unit 418 may be a floppy disk, magnetic tape, compact disk, DVD, optical storage disk, and/any other computer data storage device. Removable storage drive 414 may read from and/or write to removable storage unit 418.

Secondary memory 410 may include other means, devices, components, instrumentalities or other approaches for allowing computer programs and/or other instructions and/or data to be accessed by computer system 400. Such means, devices, components, instrumentalities or other approaches may include, for example, a removable storage unit 422 and an interface 420. Examples of the removable storage unit 422 and the interface 420 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 400 may further include a communication or network interface 424. Communication interface 424 may enable computer system 400 to communicate and interact with any combination of external devices, external networks, external entities, etc. (individually and collectively referenced by reference number 428). For example, communication interface 424 may allow computer system 400 to communicate with external or remote devices 428 over communication path 426, which may be wired and/or wireless (or a combination thereof), and which may include any combination of LANs, WANs, the Internet, etc. Control logic and/or data may be transmitted to and from computer system 400 via communication path 426. In some embodiments, communication path 426 is the connection to the cloud 130, as depicted in FIG. 1. The external devices, etc. referred to by reference number 428 may be devices, networks, entities, etc. in the cloud 130.

Computer system 400 may also be any of a personal digital assistant (PDA), desktop workstation, laptop or notebook computer, netbook, tablet, smart phone, smart watch or other wearable, appliance, part of the Internet of Things (IoT), and/or embedded system, to name a few non-limiting examples, or any combination thereof.

It should be appreciated that the framework described herein may be implemented as a method, process, apparatus, system, or article of manufacture such as a non-transitory computer-readable medium or device. For illustration purposes, the present framework may be described in the context of distributed ledgers being publicly available, or at least available to untrusted third parties. One example as a modern use case is with blockchain-based systems. It should be appreciated, however, that the present framework may also be applied in other settings where sensitive or confidential information may need to pass by or through hands of untrusted third parties, and that this technology is in no way limited to distributed ledgers or blockchain uses.

Computer system 400 may be a client or server, accessing or hosting any applications and/or data through any delivery paradigm, including but not limited to remote or distributed cloud computing solutions; local or on-premises software (e.g., "on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), database as a service (DBaaS), etc.); and/or a hybrid model including any combination of the foregoing examples or other services or delivery paradigms.

Any applicable data structures, file formats, and schemas may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

Any pertinent data, files, and/or databases may be stored, retrieved, accessed, and/or transmitted in human-readable formats such as numeric, textual, graphic, or multimedia formats, further including various types of markup language, among other possible formats. Alternatively or in combination with the above formats, the data, files, and/or databases may be stored, retrieved, accessed, and/or transmitted in binary, encoded, compressed, and/or encrypted formats, or any other machine-readable formats.

Interfacing or interconnection among various systems and layers may employ any number of mechanisms, such as any number of protocols, programmatic frameworks, floorplans, or application programming interfaces (API), including but not limited to Document Object Model (DOM), Discovery Service (DS), NSUserDefaults, Web Services Description Language (WSDL), Message Exchange Pattern (MEP), Web Distributed Data Exchange (WDDX), Web Hypertext Application Technology Working Group (WHATWG) HTML5 Web Messaging, Representational State Transfer (REST or RESTful web services), Extensible User Interface Protocol (XUP), Simple Object Access Protocol (SOAP), XML Schema Definition (XSD), XML Remote Procedure Call (XML-RPC), or any other mechanisms, open or proprietary, that may achieve similar functionality and results.

Such interfacing or interconnection may also make use of uniform resource identifiers (URI), which may further include uniform resource locators (URL) or uniform resource names (URN). Other forms of uniform and/or unique identifiers, locators, or names may be used, either exclusively or in combination with forms such as those set forth above.

Any of the above protocols or APIs may interface with or be implemented in any programming language, procedural, functional, or object-oriented, and may be compiled or interpreted. Non-limiting examples include C, C++, C#, Objective-C, Java, Scala, Clojure, Elixir, Swift, Go, Perl, PHP, Python, Ruby, JavaScript, WebAssembly, or virtually any other language, with any other libraries or schemas, in any kind of framework, runtime environment, virtual machine, interpreter, stack, engine, or similar mechanism, including but not limited to Node.js, V8, Knockout, jQuery, Dojo, Dijit, OpenUI5, AngularJS, Express.js, Backbone.js, Ember.js, DHTMLX, Vue, React, Electron, and so on, among many other non-limiting examples.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 400, main memory 408, secondary memory 410, and removable storage units 418 and 422, as well as tangible articles of manufacture embodying any combination of the foregoing. Such control logic, when executed by one or more data processing devices (such as computer system 400), may cause such data processing devices to operate as described herein.

Based on the teachings contained in this disclosure, it will be apparent to persons skilled in the relevant art(s) how to make and use embodiments of this disclosure using data processing devices, computer systems and/or computer architectures other than that shown in FIG. 4. In particular, embodiments may operate with software, hardware, and/or operating system implementations other than those described herein.

It is to be appreciated that the Detailed Description section, and not any other section, is intended to be used to interpret the claims. Other sections may set forth one or more but not all exemplary embodiments as contemplated by the inventor(s), and thus, are not intended to limit this disclosure or the appended claims in any way.

While this disclosure describes exemplary embodiments for exemplary fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries may be defined as long as the specified functions and relationships (or equivalents thereof) are appropriately performed. Also, alternative embodiments may perform functional blocks, steps, operations, methods, etc. using orderings different from those described herein.

References herein to "one embodiment," "an embodiment," "an example embodiment," "some embodiments," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

Additionally, some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

The breadth and scope of this disclosure should not be limited by any of the above-described exemplary embodiments, but should be defined only in accordance with the following claims and their equivalents

What is claimed is:

1. A method for identifying one or more base-calling locations in a sample on a flow cell comprising:
   obtaining a first plurality of flow cell images corresponding to different fluorescent wavelengths, wherein the first plurality of flow cell images represents the flow cell in one or more flow cycles, and wherein each wavelength of the different fluorescent wavelengths corresponds to a respective nucleotide base, identifying one or more DNA cluster centers in the first plurality of flow cell images by applying a spot-finding algorithm based on pixel intensity and relative color purity of the plurality of flow cell images; and generating a template by mapping a plurality of base-calling locations corresponding to the identified one or more DNA cluster centers onto the template, wherein the template is configured for registering a second plurality of flow cell images acquired of the flow cell in one or more subsequent flow cycles to the template.

2. The method of claim 1, wherein identifying the one or more DNA cluster centers in the first plurality of flow cell images by applying the spot-finding algorithm is at a sub-pixel resolution.

3. The method of claim 1, wherein a wavelength of an optical signal detected at the one or more DNA cluster centers in a flow cycle correlates to a nucleotide base added to the one or more DNA cluster centers in the flow cycle.

4. The method of claim 1, wherein the template is further configured for aligning each of the second plurality of flow cell images with the template.

5. The method of claim 1, wherein the pixel intensity comprises a corresponding pixel intensity at each of the one or more DNA cluster centers.

6. The method of claim 5, wherein the corresponding pixel intensity is determined based on a comparison of a set of channel intensities at the corresponding DNA cluster center of the one or more DNA cluster centers, each channel intensity in the set of channel intensities corresponding to a respective different fluorescent wavelength.

7. The method of claim 1, further comprising:

identifying one or more nucleotide bases added at each of the plurality base-calling locations in one or more subsequent flow cycles based on the template.

8. The method of claim 1, wherein mapping the plurality of base-calling locations corresponding to the identified DNA cluster centers onto the template comprises generating coordinates of the plurality of base-calling locations in a common coordinate system.

9. A system for identifying one or more base-calling locations in a sample on a flow cell, the system comprising:

data storage; and one or more processors coupled to the data storage and configured to:

obtain a first plurality of flow cell images corresponding to different fluorescent wavelengths, wherein the first plurality of flow cell images represents the flow cell in one or more flow cycles, and wherein each wavelength of the different fluorescent wavelengths corresponds to a respective nucleotide base;

identifying one or more DNA cluster centers in the first plurality of flow cell images by applying a spot-finding algorithm based on pixel intensity and relative color purity of the plurality of flow cell images, and generating a template by mapping a plurality of base-calling locations corresponding to the identified one or more DNA cluster centers onto the template, wherein the template is configured for registering a second plurality of flow cell images acquired of the flow cell in one or more subsequent flow cycles to the template.

10. The system of claim 9, wherein identifying the one or more DNA cluster centers in the first plurality of flow cell images by applying the spot-finding algorithm is at a sub-pixel resolution.

11. The system of claim 9, wherein a wavelength of an optical signal detected at the one or more DNA cluster centers in a flow cycle correlates to a nucleotide base added to the one or more DNA cluster centers in the flow cycle.

12. The system of claim 9, wherein the template is further configured for aligning each of the second plurality of flow cell images with the template.

13. The system of claim 9, wherein the pixel intensity comprises a corresponding pixel intensity at each of the one or more DNA cluster centers.

14. The system of claim 13, wherein the corresponding pixel intensity is determined based on a comparison of a set of channel intensities at the corresponding DNA cluster center of the one or more DNA cluster centers, each channel intensity in the set of channel intensities corresponding to a respective different fluorescent wavelength.

15. The system of claim 9, wherein the operations further comprise:

identifying one or more nucleotide bases added at each of the plurality base-calling locations in one or more subsequent flow cycles based on the template.

16. The system of claim 9, wherein mapping the plurality of base-calling locations corresponding to the identified DNA cluster centers onto the template comprises generating coordinates of the plurality of base-calling locations in a common coordinate system.

17. A non-transitory computer readable storage medium having computer readable code thereon, the non-transitory computer readable medium including instructions configured to cause a computer system to perform operations comprising:

obtaining a first plurality of flow cell images corresponding to different fluorescent wavelengths, wherein the first plurality of flow cell images represents the flow cell in one or more flow cycles, and wherein each wavelength of the different fluorescent wavelengths corresponds to a respective nucleotide base;

identifying one or more DNA cluster centers in the first plurality of flow cell images by applying a spot-finding algorithm based on pixel intensity and relative color purity of the plurality of flow cell images, and generating a template by mapping a plurality of base-calling locations corresponding to the identified one or more DNA cluster centers onto the template, wherein the template is configured for registering a second plurality of flow cell images acquired of the flow cell in one or more subsequent flow cycles to the template.

18. The non-transitory computer readable storage medium of claim 17, wherein the spot-finding algorithm detects the one or more DNA cluster centers at a sub-pixel resolution.

19. The non-transitory computer readable storage medium of claim 17, wherein a wavelength of an optical signal detected at the one or more DNA cluster centers in a flow cycle correlates to a nucleotide base added to the one or more DNA cluster centers in the flow cycle.

20. The non-transitory computer readable storage medium of claim 17, wherein mapping the plurality of base-calling locations corresponding to the identified DNA cluster centers onto the template comprises generating coordinates of the plurality of base-calling locations in a common coordinate system.

* * * * *

UNITED STATES PATENT AND TRADEMARK OFFICE
CERTIFICATE OF CORRECTION

PATENT NO. : 11,915,444 B2
APPLICATION NO. : 17/854042
DATED : February 27, 2024
INVENTOR(S) : Zhou et al.

Page 1 of 1

It is certified that error appears in the above-identified patent and that said Letters Patent is hereby corrected as shown below:

In the Claims

In Column 17, Claim 9, Line 56, delete "images," and insert -- images; --, therefor.

In Column 18, Claim 17, Line 44, delete "images," and insert -- images; --, therefor.

Signed and Sealed this
Twenty-third Day of September, 2025

John A. Squires
*Director of the United States Patent and Trademark Office*